United States Patent
Buerger et al.

(10) Patent No.: US 10,937,170 B2
(45) Date of Patent: Mar. 2, 2021

(54) APPARATUS FOR ADAPTIVE CONTOURING OF A BODY PART

(71) Applicant: KONINKLIJKE PHILIPS N.V., Eindhoven (NL)

(72) Inventors: Christian Buerger, Hamburg (DE); Jens Wiegert, Aachen (DE); Steffen Renisch, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 47 days.

(21) Appl. No.: 16/332,859

(22) PCT Filed: Sep. 21, 2017

(86) PCT No.: PCT/EP2017/073964
§ 371 (c)(1),
(2) Date: Mar. 13, 2019

(87) PCT Pub. No.: WO2018/055066
PCT Pub. Date: Mar. 29, 2018

(65) Prior Publication Data
US 2019/0251693 A1 Aug. 15, 2019

(30) Foreign Application Priority Data
Sep. 21, 2016 (EP) .................................. 16189826

(51) Int. Cl.
*G06T 7/149* (2017.01)
*G06T 7/12* (2017.01)
(Continued)

(52) U.S. Cl.
CPC ................ *G06T 7/149* (2017.01); *A61B 6/00* (2013.01); *G06T 7/12* (2017.01); *G06T 7/174* (2017.01);
(Continued)

(58) Field of Classification Search
CPC ........... G06T 7/149; G06T 7/12; G06T 7/174; G06T 7/215; A61B 6/00
See application file for complete search history.

(56) References Cited

U.S. PATENT DOCUMENTS

2008/0100612 A1  5/2008 Dastmalchi
2008/0123927 A1* 5/2008 Miga ....................... G06T 7/344
382/131

(Continued)

FOREIGN PATENT DOCUMENTS

WO   2005008587   1/2005
WO   2011073820   6/2011
(Continued)

OTHER PUBLICATIONS

Ecabert: "Automatic Model-Based Segmentation of the Heart in CT Images", IEEE Transactions on Medical Imaging, vol. 27, No. 9, Sep. 2008.

*Primary Examiner* — Jingge Wu (57) ABSTRACT

The present invention relates to an apparatus for adaptive contouring of a body part. It is described to provide (210) at least one image; wherein, the at least one image comprises a first image comprising image data of a body part. An initial automatic model based segmentation of image data of the body part in the first image is determined (220). Final segmentation data of the body part is determined (230) in response to a modification of the initial automatic model based segmentation. An updated model based segmentation can be applied (240) on the basis of the initial automatic model based segmentation and the final segmentation data.

20 Claims, 3 Drawing Sheets

(51) Int. Cl.
*A61B 6/00* (2006.01)
*G06T 7/174* (2017.01)

(52) U.S. Cl.
CPC ............... *G06T 2207/20092* (2013.01); *G06T 2207/20101* (2013.01); *G06T 2207/30004* (2013.01); *G06T 2207/30196* (2013.01)

(56) References Cited

U.S. PATENT DOCUMENTS

| | | | |
|---|---|---|---|
| 2009/0226069 A1* | 9/2009 | Razzaque | A61B 34/20 |
| | | | 382/131 |
| 2011/0317896 A1 | 12/2011 | Huber | |
| 2012/0087561 A1 | 4/2012 | Guetter | |
| 2013/0135305 A1* | 5/2013 | Bystrov | G06T 7/11 |
| | | | 345/420 |
| 2017/0143427 A1* | 5/2017 | Grady | A61B 34/10 |
| 2017/0213339 A1* | 7/2017 | Hibbard | G06K 9/6267 |
| 2018/0061059 A1* | 3/2018 | Xu | G06N 3/084 |
| 2018/0174311 A1* | 6/2018 | Kluckner | G06K 9/6259 |
| 2018/0270474 A1* | 9/2018 | Liu | A61B 6/032 |
| 2018/0336689 A1* | 11/2018 | Kabus | G06T 7/337 |
| 2019/0021681 A1* | 1/2019 | Kohli | G06T 7/11 |

FOREIGN PATENT DOCUMENTS

| | | |
|---|---|---|
| WO | 2012/069965 | 5/2012 |
| WO | 2015090459 | 6/2015 |

* cited by examiner

APPARATUS FOR ADAPTIVE CONTOURING OF A BODY PART

CROSS REFERENCE TO RELATED APPLICATIONS

This application is the U.S. National Phase application under 35 U.S.C. § 371 of International Application No. PCT/EP2017/073964 filed Sep. 21, 2017, published as WO 2018/055066 on Mar. 29, 2018, which claims the benefit of European Patent Application Number 16189826.7 filed Sep. 21, 2016. These applications are hereby incorporated by reference herein.

FIELD OF THE INVENTION

The present invention relates to an apparatus for adaptive contouring of a body part, a system for adaptive contouring of a body part, and to a method for adaptive contouring of a body part, as well as to a computer program element and a computer readable medium.

BACKGROUND OF THE INVENTION

When providing an automated segmentation of an organ, a user sometimes desires to modify the segmentation result. For example, in radiotherapy treatment planning (RTP), a segmentation of the planning target volume (PTV) is commonly modified by the user before the actual treatment planning is executed (e.g. due to suspected subclinical spread of the disease). Such modifications might include a global dilation of the segmentation result to include a safety margin around the PTV, or any other local modifications as desired by the current user. However, in the next planning session for the same patient or a different patient, the user needs to manually modify the repeated automated segmentation result again, which makes the workflow tedious and inefficient.

US2012/087561A1 describes that a method for identifying a region of interest within a time sequence of images includes acquiring a time sequence of images comprising a plurality of image frames. Image segmentation is performed to segment a region of interest (ROI) from within each of the plurality of image frames of the time sequence of images. Manual edits are received for the ROI within one or more of the plurality of image frames. The manual edits are propagated to other image frames of the plurality of images. An extent to which each of the manual edits are propagated to other image frames is dependent upon a transformation function or deformation field used to propagate the manual edits and a weighing factor that is influenced by a distance in time between the other image frames and the frames that have been manually edited.

US2008/100612A1 describes an OCT imaging system user interface for efficiently providing relevant image displays to the user. These displays are used during image acquisition to align patients and verify acquisition image quality. During image analysis, these displays indicate positional relationships between displayed data images, automatically display suspicious analysis, automatically display diagnostic data, simultaneously display similar data from multiple visits, improve access to archived data, and provide other improvements for efficient data presentation of relevant information.

WO2012/069965A1 describes that a radiation therapy planning system includes a planning module which receives a first planning image set from a diagnostic imaging apparatus and uses automatic segmentation tools or manual segmentation tools and a radiation therapy planning system to generate a first radiation therapy plan. After the first radiation therapy plan has been applied for one or more therapy sessions, a second planning image set is generated. The planning module uses a deformable image registration algorithm to register the planning image set sand generate a corresponding deformation map which is applied to segmented objects of interest (OOIs) of the segmented first planning image set to propagate the objects of interest onto the second planning image set. The deformation map is corrected in accordance with deviations between the propagated and actual OOI locations in two steps: 1) manual and/or automated corrections of the propagated OOIs are performed, such as region of interest contour corrections and/or landmark point of interest positions; 2) a corrected global deformation map is generated from these local OOI corrections. The corrected deformation map is applied to the first radiation therapy plan and an accumulated radiation map depicting the radiation accumulated in each OOI during the therapy session(s) implemented with the first radiation therapy plan.

SUMMARY OF THE INVENTION

It would be advantageous to have an improved technique for automatically segmenting a body part.

The object of the present invention is solved with the subject matter of the independent claims, wherein further embodiments are incorporated in the dependent claims.

It should be noted that the following described aspects of the invention apply also for the apparatus for adaptive contouring a body part, the system for adaptive contouring a body part, the method for adaptive contouring a body part, and for the computer program element and the computer readable medium.

In a first aspect, there is provided an apparatus for adaptive contouring of a body part, comprising:

an input unit; and
a processing unit.

The input unit is configured to provide the processing unit with at least one image. The at least one image comprises a first image comprising image data of a body part. The processing unit is configured to determine an initial automatic model based segmentation of image data of the body part in the first image. In response to a modification of the initial automatic model based segmentation the processing unit is configured to determine final segmentation data of the body part. The processing unit is configured to apply an updated automatic model based segmentation on the basis of the initial automatic model based segmentation and the final segmentation data.

In other words a model based segmentation (MBS) is used to delineate an organ in medical image(s). The segmentation could be a surface representation of a body part such as a heart, liver, kidney etc. The automatically generated segmentation is then modified, through for example a user such as a surgeon moving parts of the segmentation surface to new positions. The apparatus on the basis of the modified segmentation can then later regenerate the modified segmentation. Thus for radiotherapy treatment planning (RTP) for example, where a planning target volume (PTV) is used, a surgeon may wish to apply RTP that covers a slightly different volume than that delineated in a normal segmentation process. The surgeon's specific requirement is stored and can then automatically be reapplied to the same patient in the future, without the surgeon having to again re-modify the PTV, and indeed the surgeon can apply such a modified PTV to other patients again without having to modify the PTV.

To put this another way, a user's modifications can be remembered as deviations from an auto-segmentation and those deviations (i.e., surface distances) are added to the auto-segmentation in order to automatically take into account the initial modifications. Thus, those deviations are (i.e., surface deviations) are incorporated into the auto-segmentation (e.g. added to the auto-segmentation).

In this manner, modifications such as user modifications on an automatically segmented mesh are used in that these modifications are incorporated as mesh deformations for the next planning radiotherapy (RT) session or for the next patient in a consistent way. This saves time and significantly improves the clinical workflow.

Thus, organ segmentations can be delivered including reproducible user-specific modifications, i.e. all modifications of one specific user can be used to derive a "typical" mean modification according to the "taste" of that user. Also, organ segmentations can be delivered including patient-specific modifications, i.e. the modification required for a specific patient can be remembered to automatically allow consistent and reproducible further segmentation results of this particular patient including its patient-specific modifications.

In an example, modification of the initial automatic model based segmentation results in a revised model based segmentation, and wherein the processing unit is configured to determine the final segmentation data on the basis of the revised model based segmentation.

In other words, modification of a first segmentation results in a second segmentation. For example a three dimensional surface outline of an organ can be modified by a user in some way, through for example pulling the surface away from the its original position in some areas around the organ. In this way, a surgeon may wish e.g. for RT to be applied to a region extending further from the organ than that delineated by the original segmentation. The first segmentation is characterized by certain data and the second (modified) segmentation is characterized by certain data, and these data can be used to enable the apparatus to automatically generate the second (modified) segmentation.

In an example, determination of the final segmentation data comprises determination of at least one deviation between the initial automatic model based segmentation and the revised model based segmentation.

In an example, determination of the final segmentation data comprises determination of at least one distance between the initial automatic model based segmentation and the revised model based segmentation.

Thus a deviation between meshes can be remembered or stored as a distance, however such a deviation could be remembered or stored as a scaling factor or scaling factors relating to a global deviation of the complete mesh or specific scaling factor relating to local deviations of sections of the mesh.

In this manner, e.g. a simple distance metric between the first segmentation and the second segmentation can be used in automatically determining a new segmentation that accounts for user modifications.

In an example, the initial automatic model based segmentation comprises at least two areal segments, the at least two areal segments comprising a first areal segment and a second areal segment sharing one common boundary. The revised model based segmentation comprises at least two areal segments that correlate with the at least two areal segments of the initial automatic model based segmentation. The at least two areal segments of the revised model based segmentation comprising a first areal segment and a second areal segment sharing one common boundary. The determined at least one deviation comprises at least one distance that extends from the boundary between the first and second areal segments on the initial automatic model based segmentation and the first and second areal segments on the revised model based segmentation.

In this manner, by considering boundaries between areal parts of segmented surfaces, a new updated segmentation can be automatically generated, that takes into account user modifications, and where the updated segmentation will not have overlapping segmented surfaces. This is because by considering boundaries between areal parts of segmented surfaces continuity of surfaces is enabled, such that the segments do not overlap. To put this another way, by considering boundaries between areal segments the areal segments can be forced to be joined at that boundary. Then, when that boundary is moved the areal segments maintain their join at that boundary and in this way, the areal segments do not overlap as a consequence of the movement.

In an example, the processing unit is configured to determine the final segmentation data as the model based segmentation parameters that result in the revised model based segmentation.

In other words, a user modifies a segmented surface to provide a new segmented surface. The processing unit then iterates, through an energy minimization routine such as a Monte-Carlo routine, the segmentation parameters until it can recreate the modified segmented surface.

In an example, the modification of the initial automatic model based segmentation comprises at least one deviation from the initial automatic model based segmentation and wherein the final segmentation data are determined on the basis of the at least one deviation from the initial model based segmentation.

In other words, a user may just indicate one or more deviations from an original segmentation surface as "modifications". The processing unit on the basis of the deviations, then is enabled to automatically generate a new segmentation of an organ that takes into account a surgeon's modifications.

In an example, the at least one deviation comprises at least one distance. In this manner, a user can input modifications, as for example distances from the segmented surface.

In an example, the at least one image comprises a second image comprising image data of the body part, and wherein the processing unit is configured to determine a segmentation of the body part in the second image on the basis of the updated model based segmentation.

Thus, the apparatus can apply the learned new segmentation, that takes into account a users "taste" or requirements, and apply such a segmentation to new image data of a body part.

In an example, the second image is for the same patient as for the first image.

In other words, in this manner the apparatus saves time in the treatment of a patient, where an initial user modification of a segmentation of a body part such as an organ can be automatically propagated to influence later segmentations, thus providing for more effective RTP.

In an example, the second image is for a different patient as for the first image.

Thus a surgeon's generalized requirements, for example as to how a particular organ should be treated, can be utilized for all patients without the requirement to modify segmentation data for different patients from a starting point. A surgeon may utilize the updated (modified) segmentation that was developed from a different patient, but any additional modification will be less than that required if starting from scratch.

In a second aspect, there is provided a system for adaptive contouring of a body part, comprising:
an image acquisition unit;
an apparatus for adaptive contouring of a body part according to the first aspect; and
an output unit.

The image acquisition unit is configured to acquire an image comprising image data of the body part, and the image acquisition unit is configured to provide the input unit with the image. The processing unit is configured to determine a segmentation of the image data of the body part through application of the updated model based segmentation. The output unit is configured to output data representative of the updated model based segmentation.

In this manner, a user's general "taste" or patient-specific modifications in RTP, as well as earlier corrective modifications, can automatically be incorporated back into a segmentation pipeline. Thus, a surgeons "taste" can be stored and re-applied to segmentations, for example the surgeon may wish to have an enlarged envelope around a prostate that is dilated by 5 mm everywhere (or over specific parts of the prostate) for all patients, and such a taste of the surgeon can automatically be re-applied to segmentations for all patients. Also, and similarly for a specific patient, the surgeon may wish to have a bespoke modification for that particular patient, and this modification of a segmentation can be stored and re-applied for that patient. To put this another way, an updated model based segmentation determined from previous imagery and user modifications, can be used to provide an automatically updated segmentation of a body part such as an organ that accounts for the users requirements. In this way a segmentation is automatically provided that automatically provides for modifications that would normally have to be input manually by a user such as a surgeon. Thus clinical workflow is strongly simplified, because manual modifications are either only required in a training phase or once per patient within the entire course of treatment. Future segmentations require much less, if any, user interaction because these modifications are already incorporated automatically.

In a third aspect, there is provided a method for adaptive contouring of a body part, comprising:
a) providing at least one image; wherein, the at least one image comprises a first image comprising image data of a body part;
b) determining an initial automatic model based segmentation of image data of the body part in the first image;
c) determining final segmentation data of the body part in response to a modification of the initial automatic model based segmentation; and
d) applying an updated model based segmentation on the basis of the initial automatic model based segmentation and the final segmentation data.

In an example, modification of the initial automatic model based segmentation results in a revised model based segmentation, and wherein in step c) the final segmentation data is determined on the basis of the revised model based segmentation.

According to another aspect, there is provided a computer program element controlling apparatus as previously described which, in the computer program element is executed by processing unit, is adapted to perform the method steps as previously described.

According to another aspect, there is provided a computer readable medium comprising the computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
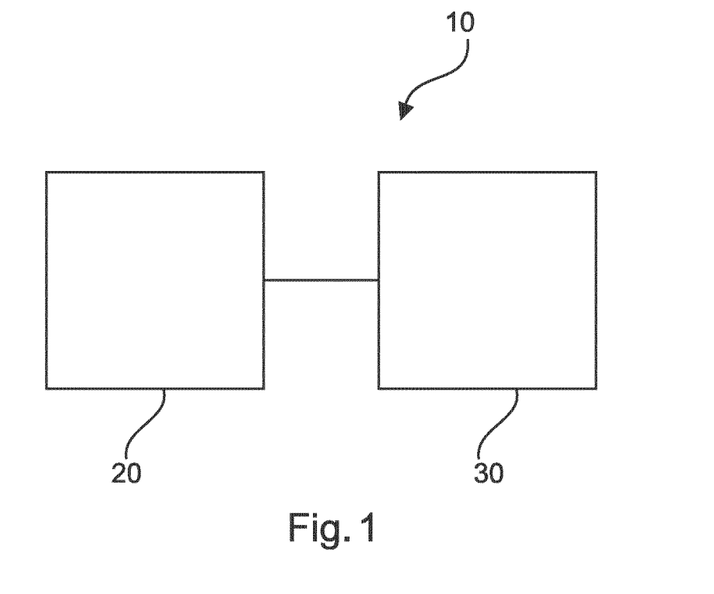
FIG. 1 shows a schematic set up of an example of an apparatus for adaptive contouring a body part.

FIG. 1 shows an example of an apparatus 10 for adaptive contouring of a body part. The apparatus 10 comprises an input unit 20, and a processing unit 30. The input unit 20 is configured to provide the processing unit 30 with at least one image. This is done via wired or wireless communication. The at least one image comprises a first image comprising image data of a body part. The processing unit 30 is configured to determine an initial automatic model based segmentation of image data of the body part in the first image. In response to a modification of the initial automatic model based segmentation the processing unit 30 is configured to determine final segmentation data of the body part. The processing unit 30 is also configured to apply an updated automatic model based segmentation on the basis of the initial automatic model based segmentation and the final segmentation data.

In an example, the input unit comprises a data storage or transfer unit configured to provide the at least one image. In other words, the apparatus can operate in an offline mode processing previously acquired imagery. In an example, the input unit can be or form part of an image acquisition unit or receive imagery from such an image acquisition unit.

In an example, mesh to mesh distances between the initial automatic model based segmentation and the modification of the initial automatic model based segmentation are stored, and can be used (or re-applied) in determining a later modified segmentation.

According to an example, modification of the initial automatic model based segmentation results in a revised model based segmentation. The processing unit 30 is configured to determine the final segmentation data on the basis of the revised model based segmentation.

According to an example, determination of the final segmentation data comprises determination of at least one deviation between the initial model based segmentation and the revised model based segmentation. The at least one deviation can be at least one distance and/or at least one scaling factor between meshes.

According to an example, the initial automatic model based segmentation comprises at least two areal segments.

The at least two areal segments comprise a first areal segment and a second areal segment sharing one common boundary. The revised model based segmentation comprises at least two areal segments that correlate with the at least two areal segments of the initial automatic model based segmentation. The at least two areal segments of the revised model based segmentation comprise a first areal segment and a second areal segment sharing one common boundary. The determined at least one distance extends from the boundary between the first and second areal segments on the initial automatic model based segmentation and the first and second areal segments on the revised model based segmentation.

According to an example, the processing unit 30 is configured to determine the final segmentation data as the model based segmentation parameters that result in the revised model based segmentation.

In an example, the processing unit is configured to iterate, through an energy minimization routine such as a Monte-Carlo routine, the segmentation parameters until it can recreate the modified segmented surface.

According to an example, the modification of the initial automatic model based segmentation comprises at least one deviation from the initial automatic model based segmentation. The final segmentation data are determined on the basis of the at least one deviation from the initial model based segmentation.

According to an example, the at least one deviation comprises at least one distance.

According to an example, the at least one image comprises a second image comprising image data of the body part. The processing unit 30 is configured to determine a segmentation of the body part in the second image on the basis of the updated model based segmentation.

According to an example, the second image is for the same patient as for the first image.

According to an example, the second image is for a different patient as for the first image.

Figure 2:
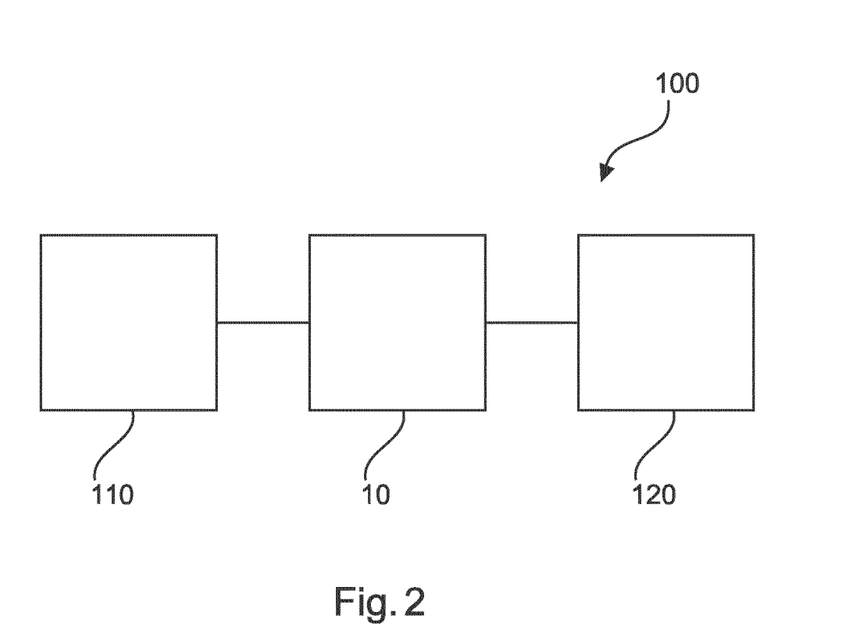
FIGS. 2 and 3 show schematic set ups of examples of a system for adaptive contouring a body part.
Figure 3:
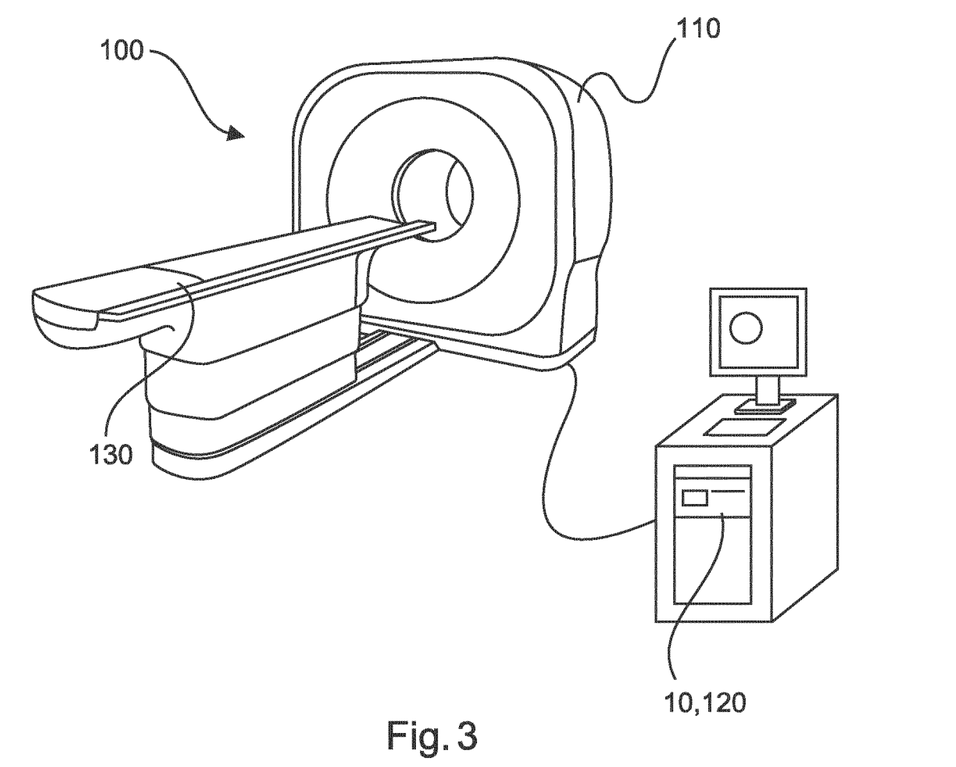

FIGS. 2 and 3 show examples of a system 100 for adaptive contouring of a body part. The system 100 comprises an image acquisition unit 110, and an apparatus 10 for adaptive contouring of a body part as discussed with respect to FIG. 1. The system 100 also comprises an output unit 120. The system 100 can comprise a table 130 on which a patient lies, which can move into the image acquisition unit 110. Parts of the apparatus 10 can be housed in the image acquisition unit 110 and/or parts of the apparatus 10 can be housed in the output unit 120. For example, the input unit 20 and processor 30 can be housed in the image acquisition unit 110 or housed in the output unit 120, which is shown in FIG. 3 as a workstation. The image acquisition unit 110 can be the input unit 20 of the apparatus 10. The image acquisition unit 110 is configured to acquire an image comprising image data of the body part. The image acquisition unit is configured to provide the input unit 20 with the image. The input unit 20 then provides the processing unit 30 with the image. These communications can be via wired or wireless communication. The processing unit 30 is configured to determine a segmentation of the image data of the body part through application of the updated model based segmentation. The output unit 120 is configured to output data representative of the updated model based segmentation.

In an example, the acquisition unit is configured to acquire the first image. However, the first image that is used to determine the updated model based segmentation could have been acquired by a different image acquisition unit.

In an example, the image acquired by the image acquisition unit is the second image.

In an example, the acquisition unit is an ultrasound probe. In an example, the acquisition unit is an X-ray scanner such as a C-arm scanner. In an example, the acquisition unit is a MRI scanner.

In an example, an image is an X-ray image. In an example, an X-ray image is formed from a number of individual X-ray images to provide a volume representation of a body part. In an example, an image is an ultrasound image. In an example, an image is an MRI image. Ultrasound and MRI images can also be three dimensional images.

In an example, the output unit is configured to display image data, for example displaying images on one or more monitors such as one or more visual display units VDUs.

In an example, the input unit 20 is the image acquisition unit 110.

Figure 4:
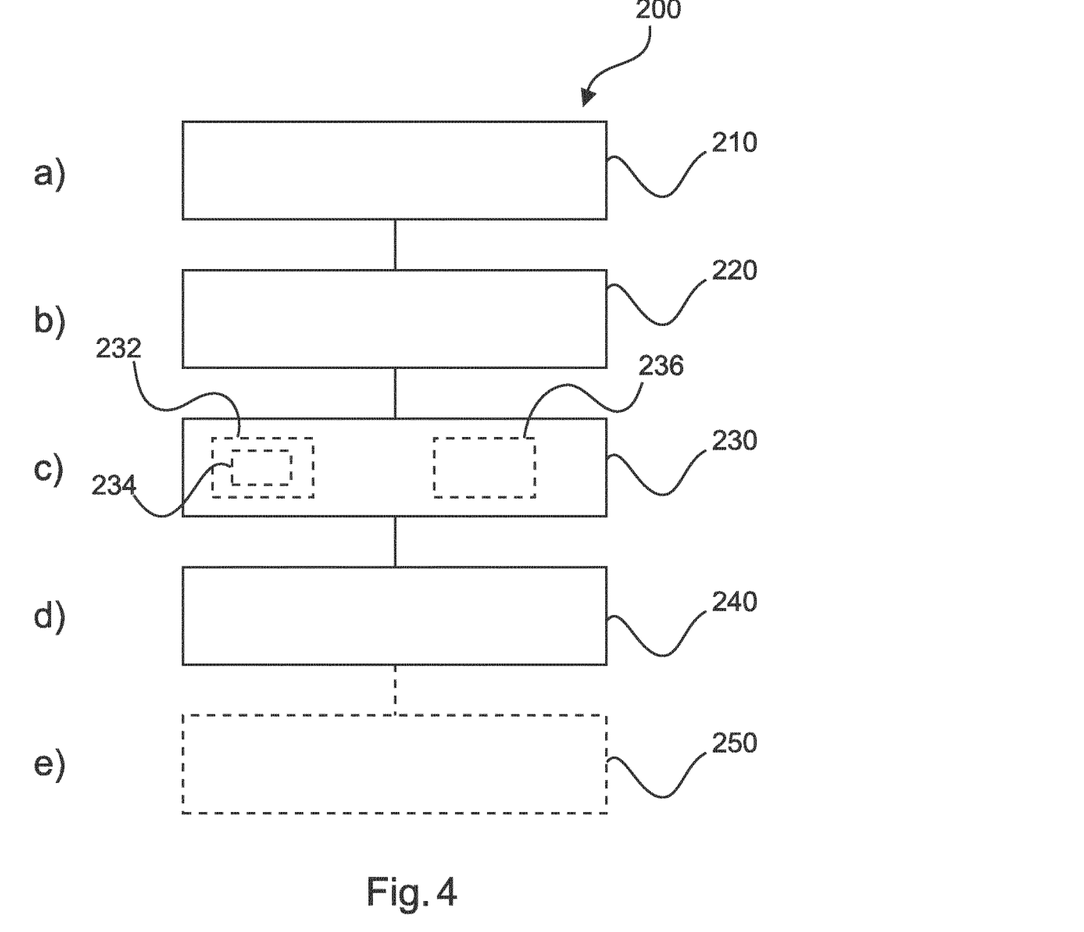
FIG. 4 shows an example of a method for adaptive contouring a body part.

FIG. 4 shows a method 200 for adaptive contouring of a body part in its basic steps. The method 200 comprises:

in a providing step 210, also referred to as step a), providing at least one image; wherein, the at least one image comprises a first image comprising image data of a body part;

in a determining step 220, also referred to as step b), determining an initial automatic model based segmentation of image data of the body part in the first image;

in a determining step 230, also referred to as step c), determining final segmentation data of the body part in response to a modification of the initial automatic model based segmentation; and in an applying step 240, also referred to as step d), applying an updated model based segmentation on the basis of the initial automatic model based segmentation and the final segmentation data.

In an example at step a) a processing unit is provided with the at least one image, and the processing unit carries out steps b) and c). However, in an example a different processor can carry out step d), or the same processor that carried out steps b) and c) can carry out step d).

According to an example, modification of the initial automatic model based segmentation results in a revised model based segmentation, and wherein in step c) the final segmentation data is determined on the basis of the revised model based segmentation.

In an example, step c) comprises step c1) determining 232 at least one deviation between the initial automatic model based segmentation and the revised model based segmentation.

In an example, the at least one deviation comprises at least one distance. In an example, the at least one deviation comprises at least one scaling factor.

In an example, the initial automatic model based segmentation comprises at least two areal segments, the at least two areal segments comprising a first areal segment and a second areal segment sharing one common boundary. The revised model based segmentation comprises at least two areal segments that correlate with the at least two areal segments of the initial automatic model based segmentation. The at least two areal segments of the revised model based segmentation comprise a first areal segment and a second areal segment sharing one common boundary. In the method step c1) comprises determining 234 at least one distance that extends from the boundary between the first and second areal segments on the initial automatic model based segmentation and the first and second areal segments on the revised model based segmentation.

In an example, step c) comprises determining 236 the final segmentation data as the model based segmentation parameters that result in the revised model based segmentation.

In an example, the modification of the initial automatic model based segmentation comprises at least one deviation from the initial automatic model based segmentation and in step c) the final segmentation data are determined on the basis of the at least one deviation from the initial model based segmentation.

In an example, the at least one deviation comprises at least one distance.

In an example, the at least one image comprises a second image comprising image data of the body part. The method then comprises step e), determining 250 a segmentation of the body part in the second image on the basis of the updated model based segmentation.

Figure 5:
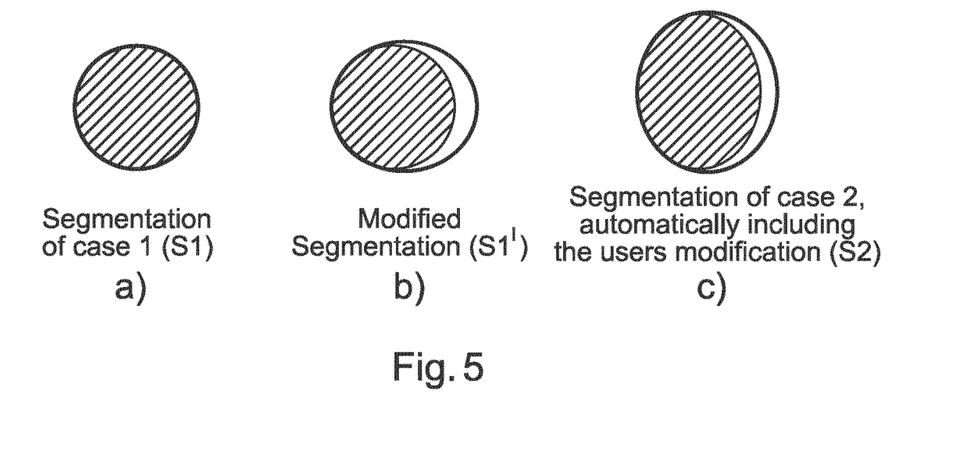
FIG. 5 shows an example of a workflow for adaptive contouring a body part.

The apparatus, system and method are now described in more detail, where reference is also made to FIG. 5.

Model Based Segmentation

The body part, for example the heart, is segmented in the X-ray image (or ultrasound image/MRI image/CT image). The segmentation of the image provides the outlines of the heart in the X-ray image volume.

In more detail, the model-based segmentation of for example the heart in the X-ray image comprises a mean model, e.g. a triangular mesh consisting of N points and T triangles connecting the points. The initial shape describes for example an average or typical shape. The model is then adapted to an image in several steps. First, the general position (for example the center-of-gravity) and orientation are determined, and the mesh is placed accordingly in the image. During model training each triangle had learned which specific image features it should search for. During adaptation, each triangle then searches for these image features, resulting in a set of attracting forces (from which the so-called external energy is derived). Based on this external energy, the model is successively adapted by estimating parameters of global or regional affine transformations (the energy is minimized). In a final step, local deformations are allowed based on the external forces. At the same time, a so-called internal energy penalizes too large deviations from the mean shape. After multiple iterations, the shape of the mesh has been adapted to the image. Because it is known which mesh parts belong to which anatomical structures, this adds anatomical context to the image. A segmentation algorithm, applied to CT images but which can also be applied here to ultrasound images/MRI images, is discussed in detail in the paper by Ecabert el al., Automatic Model-Based Segmentation of the Heart in CT Images, IEEE Transactions on Medical Imaging, Vol. 27, No. 9, Sep. 2008, 1189-1201.

FIG. 5 shows a workflow for adaptive contouring of a body part. At the step shown in (a) segmentation of an organ is carried out. For each triangle on the mesh (black outline) aligns with the boundary of the organ of interest (inner grey area). At step (b), the user has modified the mesh as part of RTP. In this example, the mesh has been dilated towards the right. The apparatus, system and method then automatically enables the manual modification to be re-applied to the organ segmentation. This is shown at step (c). This shows that when segmenting the next case 2, the mesh deformation between (a) and (b) has been incorporated into the adaptation pipeline as a typical user modification, so that the automated result already incorporates such changes. Note that here the mesh deformation is presented as a simple scaling to the horizontal direction. More advanced deformations such as organ-scale dependent distances, advanced local modifications or considering local curvatures/multiple organs and contours are possible, too. Thus, the scaling as described here is one way of "remembering" user modifications, with computing surface distances (as described above) forming another way of "remembering" such user modifications.

With continued reference to FIG. 5, in more detail the workflow accounts for modifications that might be classified into the users "taste" on the one hand (reflecting changes to adapt the segmentation to his general way of interpreting images of patients in general) and, on the other hand, corrective modifications reflecting corrections for a particular application of the segmentation to current and further images of a particular patient. To account for this, such user modifications are learnt with respect to the automated segmentation result. This is carried out using the following steps: First, the Model-Based Segmentation (MBS) is executed as usual, and a segmentation S1 of the organ of interest is delivered (FIG. 5a). Second, the user modifies the segmentation result as desired, leading to a segmentation S1' (FIG. 5b). Third, surface deviations are computed (e.g. in form of surface distances such as one signed distance value for each triangle) between S1 and S1'. Fourth, when applying the segmentation of another image of an adaptive treatment or of the next patient, those distances are used to provide an updated segmentation. In other words, the new (updated) segmentation uses the user input distances and the new segmentation incorporates these distances in providing a new segmentation, and the mesh is modified on the basis of these distances rather than the original organ outline. This will lead to an automated segmentation S2 that already incorporates the distances S1-S1', i.e. the previous user modification from S1 (FIG. 5c).

To summarize the workflow shown in FIG. 5, model-based segmentation (MBS) using triangulated surface meshes is used to robustly and accurately delineate organs in medical images. Segmentation works by finding target points in image search regions centered at each mesh triangle, followed by adapting the model mesh to all target points (using model-based regularization). However, for several applications the segmentation result might need to be modified manually. For example, in radiotherapy treatment planning (RTP), a segmentation of the planning target volume (PTV) is commonly modified by the user before computing the treatment plan. However, this modification needs to be applied every single time consistently e.g. for adaptive radiation therapy, and for consistency reasons it is also likely that it needs to be applied to other patients requiring the same contouring by this user or institution. Therefore, the workflow shown in FIG. 5 enables a user's modifications to be remembered. With this approach, the user's general "taste", as earlier corrective modifications, are learnt and these are incorporated them back into the segmentation pipeline, for example as an application of remembered surface deviations as a post-processing step. This strongly simplifies the clinical workflow because manual modifications ideally are then either only required in a training phase or once per patient within the entire course of the treatment, and future segmentations will require much less user interaction because these modifications are already incorporated automatically.

It will be appreciated that while the above workflow relates to model-based segmentation of a 3D volume, it is possible to apply this to other X-ray or ultrasound images (or indeed MRI images). For example, images can be acquired in x-plane mode, i.e. two orthogonal ultrasound slices are recorded, and segmentation applied.

The apparatus, system and method is of particular interest for RTP, especially for adaptive RT. When a treatment plan for a patient is generated, the segmentation of the PTV is commonly manually generated by the physician before executing the treatment planning software. This commonly needs to be done every single time and is hence very time-consuming. The apparatus, system and method described here allows (1) automatic segmentation of the target structure followed by (2) incorporation of manual user interactions of the physician which are tied to the initial segmentation generated in (1). In other words, user interactions are only allowed on the auto-segmented mesh, so that the modifications of that user can be incorporated as mesh deformations for the next planning session or the next patient in a consistent way. This saves time and significantly improves the clinical workflow. This also leads to the following: First, organ segmentations can be delivered including reproducible user-specific modifications, i.e. all modifications of one specific user can be used to derive a "typical" mean modification according to the "taste" of that user. Second, organ segmentations can be delivered including patient-specific modifications, i.e. the modification required for a specific patient can be remembered to automatically allow consistent and reproducible further segmentation results of this particular patients including its patient-specific modifications.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for adaptive contouring of a body part, comprising:
an input unit comprising a non-transitory computer-readable storage medium adapted to store and transfer data;
a processing unit;
wherein, the input unit is configured to provide the processing unit with at least two images;
wherein, the at least two images comprises a first image comprising image data of a body part and a second image comprising image data of the body part;
wherein, the processing unit is configured to determine an initial automatic model based segmentation of image data of the body part in the first image to provide a segmentation surface representation of the body part in the first image;
wherein, in response to a modification of the initial automatic model based segmentation, the modification comprising user based movement of at least one part of the segmentation surface to at least one new position to result in a revised model based segmentation to provide a revised segmentation surface representation of the body part in the first image, the processing unit is configured to determine final segmentation data of the body part on a basis of at least one deviation between the segmentation surface of the initial automatic model based segmentation and the revised segmentation surface of the revised model based segmentation; and
wherein, the processing unit is configured to apply an updated automatic model based segmentation to image data of the body part in the second image on the basis of the initial automatic model based segmentation and the final segmentation data to provide a segmentation surface representation of the body part in the second image.

2. The apparatus according to claim 1, wherein the segmentation surface of the initial automatic model based segmentation comprises at least two areal segments, the at least two areal segments comprising a first areal segment and a second areal segment sharing one common boundary, and wherein the revised segmentation surface of the revised model based segmentation comprises at least two areal segments that correspond to the at least two areal segments of the initial automatic model based segmentation, the at least two areal segments of the revised model based segmentation comprising a first areal segment and a second areal segment sharing one common boundary, and wherein the determined at least one deviation comprises at least one distance that extends from the boundary between the first and second areal segments on the segmentation surface of the initial automatic model based segmentation and the first and second areal segments on the revised segmentation surface of the revised model based segmentation.

3. The apparatus according to claim 1, wherein the processing unit is configured to determine the final segmentation data as the model based segmentation parameters that result in the revised model based segmentation.

4. The apparatus according to claim 1, wherein the modification of the initial automatic model based segmentation comprises at least one deviation from the initial automatic model based segmentation and wherein the final segmentation data are determined on the basis of the at least one deviation from the initial model based segmentation.

5. The apparatus according to claim 4, wherein the at least one deviation comprises at least one distance.

6. The apparatus according to claim 1, wherein the second image is for the same patient as for the first image.

7. The apparatus according to claim 1, wherein the second image is for a different patient as for the first image.

8. A system for adaptive contouring of a body part, comprising:
an image acquisition unit comprising a device that acquires image data of a body part;
an apparatus for adaptive contouring of a body part comprising: an input unit comprising a non-transitory computer-readable storage medium adapted to store and transfer data;
a processing unit;
wherein, the input unit is configured to provide the processing unit with at least two images;
wherein, the at least two images comprises a first image comprising image data of a body part and a second image comprising image data of the body part;
wherein, the processing unit is configured to determine an initial automatic model based segmentation of image data of the body part in the first image to provide a segmentation surface representation of the body part in the first image;
wherein, in response to a modification of the initial automatic model based segmentation, the modification comprising user based movement of at least one part of the segmentation surface to at least one new position to result in a revised model based segmentation to provide a revised segmentation surface representation of the body part in the first image, the processing unit is configured to determine final segmentation data of the body part on a basis of at lease one deviation between the segmentation surface of the initial automatic model based segmentation and the revised segmentation surface of the revised model based segmentation; and wherein, the processing unit is configured to apply an updated automatic model based segmentation to image data of the body part in the second image on the basis of the initial automatic model based segmentation and the final segmentation data to provide a segmentation surface representation of the body part in the second image; and a workstation;
wherein, the image acquisition unit is configured to acquire an image comprising image data of the body part, and to provide the input unit with the image; and
wherein, the processing unit is configured to determine a segmentation of the image data of the body part through application of the updated model based segmentation; and
wherein, the workstation is configured to output data representative of the updated model based segmentation.

9. A method for adaptive contouring of a body part, comprising:
a) providing at least one image; wherein, the at least one image comprises a first image comprising image data of a body part and a second image comprising image data of the body part;
b) determining an initial automatic model based segmentation of image data of the body part in the first image to provide a segmentation surface representation of the body part in the first image;
c) determining final segmentation data of the body part in response to a modification of the initial automatic model based segmentation, the modification comprising a user moving at least one part of the segmentation surface to at least one new position to result in a revised model based segmentation to provide a revised segmentation surface representation of the body part in the first image, wherein the final segmentation data is determined on a basis of at least one deviation between the segmentation surface of the initial automatic model based segmentation and the revised segmentation surface of the revised model based segmentation; and
d) applying an updated model based segmentation to image data of the body part in the second image on a basis of the initial automatic model based segmentation and the final segmentation data to provide a segmentation surface representation of the body part in the second image.

10. The system according to claim 8, wherein the segmentation surface of the initial automatic model based segmentation comprises at least two areal segments, the at least two areal segments comprising a first areal segment and a second areal segment sharing one common boundary, and wherein the revised segmentation surface of the revised model based segmentation comprises at least two areal segments that correspond to the at least two areal segments of the initial automatic model based segmentation, the at least two areal segments of the revised model based segmentation comprising a first areal segment and a second areal segment sharing one common boundary, and wherein the determined at least one deviation comprises at least one distance that extends from the boundary between the first and second areal segments on the segmentation surface of the initial automatic model based segmentation and the first and second areal segments on the revised segmentation surface of the revised model based segmentation.

11. The system according to claim 8, wherein the processing unit is configured to determine the final segmentation data as the model based segmentation parameters that result in the revised model based segmentation.

12. The apparatus according to claim 8, wherein the modification of the initial automatic model based segmentation comprises at least one deviation from the initial automatic model based segmentation and wherein the final segmentation data are determined on the basis of the at least one deviation from the initial model based segmentation.

13. The system according to claim 12, wherein the at least one deviation comprises at least one distance.

14. The system according to claim 8, wherein the second image is for the same patient as for the first image.

15. The system according to claim 8, wherein the second image is for a different patient as for the first image.

16. An apparatus, comprising:
a processor;
a non-transitory computer-readable storage medium that stores instructions, which when executed by the processor cause the processor to:
provide at least one image, wherein, the at least one image comprises a first image comprising image data of a body part and a second image comprising image data of the body part;
determines an initial automatic model based segmentation of image data of the body part in the first image to provide a segmentation surface representation of the body part in the first image;
determine a final segmentation data of the body part in response to a modification of the initial automatic model based segmentation, the modification comprising a user moving at least one part of the segmentation surface to at least one new position to result in a revised model based segmentation to provide a revised segmentation surface representation of the body part in the first image, wherein the final segmentation data is determined on a basis of at least one deviation between the segmentation surface of the initial automatic model based segmentation and the revised segmentation surface of the revised model based segmentation; and
apply an updated model based segmentation to image data of the body part in the second image on a basis of the initial automatic model based segmentation and the final segmentation data to provide a segmentation surface representation of the body part in the second image.

17. The apparatus according to claim 16, wherein the segmentation surface of the initial automatic model based segmentation comprises at least two areal segments, the at least two areal segments comprising a first areal segment and a second areal segment sharing one common boundary, and wherein the revised segmentation surface of the revised model based segmentation comprises at least two areal segments that correspond to the at least two areal segments of the initial automatic model based segmentation, the at least two areal segments of the revised model based segmentation comprising a first areal segment and a second areal segment sharing one common boundary, and wherein the determined at least one deviation comprises at least one distance that extends from the boundary between the first and second areal segments on the segmentation surface of the initial automatic model based segmentation and the first and second areal segments on the revised segmentation surface of the revised model based segmentation.

18. The apparatus according to claim 17, wherein the instructions, when executed by the processor is further configured to determine the final segmentation data as the model based segmentation parameters that result in the revised model based segmentation.

19. The apparatus according to claim 16, wherein the modification of the initial automatic model based segmentation comprises at least one deviation from the initial automatic model based segmentation and wherein the final segmentation data are determined on the basis of the at least one deviation from the initial model based segmentation.

20. The apparatus according to claim 19, wherein the at least one deviation comprises at least one distance.

* * * * *